United States Patent
Moerman

(10) Patent No.: US 6,706,049 B2
(45) Date of Patent: Mar. 16, 2004

(54) CAP FOR A LANCING DEVICE

(75) Inventor: Piet Moerman, St. Martens-Latem (BE)

(73) Assignee: Inverness Medical Limited, Inverness (GB)

(*) Notice: Subject to any disclaimer, the term of this patent is extended or adjusted under 35 U.S.C. 154(b) by 33 days.

(21) Appl. No.: 09/877,514

(22) Filed: Jun. 8, 2001

(65) Prior Publication Data
US 2002/0016606 A1 Feb. 7, 2002

Related U.S. Application Data
(60) Provisional application No. 60/261,513, filed on Jan. 12, 2001, and provisional application No. 60/210,808, filed on Jun. 9, 2000.

(51) Int. Cl.[7] ............................................. A61B 17/14
(52) U.S. Cl. .................. 606/181; 606/185; 604/164.06
(58) Field of Search ................................. 606/181, 182, 606/185, 188; 604/164.06

(56) References Cited

U.S. PATENT DOCUMENTS

| | | | |
|---|---|---|---|
| 5,324,303 A | 6/1994 | Strong et al. ............... | 606/181 |
| 5,402,798 A | 4/1995 | Swierczek et al. | |
| 5,423,847 A | 6/1995 | Strong et al. ............... | 606/182 |
| 5,547,702 A | 8/1996 | Gleisner ..................... | 427/2.13 |
| 5,569,286 A | 10/1996 | Peckham et al. ........... | 606/181 |
| 5,580,794 A | 12/1996 | Allen ......................... | 436/169 |
| 5,628,764 A | 5/1997 | Schraga ..................... | 606/182 |
| 5,709,699 A * | 1/1998 | Warner ....................... | 606/181 |
| 5,730,753 A * | 3/1998 | Morita ........................ | 600/583 |
| 5,797,942 A | 8/1998 | Schraga ..................... | 606/182 |
| 5,837,546 A | 11/1998 | Allen et al. ................. | 436/169 |
| 5,872,713 A | 2/1999 | Douglas et al. ......... | 364/413.09 |
| 5,879,367 A | 3/1999 | Latterell et al. ............. | 606/181 |
| 5,916,230 A | 6/1999 | Brenneman et al. ........ | 606/172 |
| 6,053,930 A | 4/2000 | Ruppert ..................... | 606/181 |
| 6,056,765 A * | 5/2000 | Bajaj et al. ................ | 606/181 |
| 6,071,249 A * | 6/2000 | Cunningham et al. ...... | 600/578 |
| 6,093,156 A | 7/2000 | Cunningham et al. ...... | 600/573 |
| 6,132,449 A * | 10/2000 | Lum et al. .................. | 606/181 |
| 6,197,040 B1 | 3/2001 | LeVaughn et al. .......... | 606/182 |
| 6,203,504 B1 | 3/2001 | Latterell et al. ............ | 600/576 |
| 6,210,420 B1 | 4/2001 | Mauze et al. ............... | 606/182 |
| 6,283,982 B1 | 9/2001 | Levaughn et al. .......... | 606/172 |
| 6,491,709 B2 * | 12/2002 | Sharma et al. .............. | 606/181 |
| 2002/0130042 A1 * | 9/2002 | Moerman et al. ....... | 204/403.01 |
| 2002/0198444 A1 | 12/2002 | Uchigaki et al. | |

FOREIGN PATENT DOCUMENTS

| | | |
|---|---|---|
| EP | 0783868 A1 | 7/1997 |
| WO | WO 01/28423 | 4/2001 |

OTHER PUBLICATIONS

Amira Medical "At Last Blood Glucose System User's Manual" (1999).*
Amira Medical. "At Last™ Blood Glucose System User's Manual" (1999).
Miles Incorporated. "Glucolet® Automatic Lancing Device for Obtaining Blood [User's Guide]" (1986).
Therasense. "FreeStyle™ Blood Glucose Monitoring System Owner's Booklet" (2000).

* cited by examiner

*Primary Examiner*—John J. Calvert
*Assistant Examiner*—Shaun R Hurley

(57) ABSTRACT

A cap for a lancing device for lancing dermal tissue is provided. The cap includes a cap body having a proximal end for connecting to the distal end of the housing of the lancing device and a contact ring attached to the distal end of the cap body. The contact ring includes an opening for a portion of the lancet of the lancing device to pass therethrough. The contact ring has a multi-contoured surface oriented generally about an axis distinct from the axis of motion of the lancet. The multi-contoured surface is designed to pressure the dermal tissue to facilitate expression of a fluid sample after lancing the dermal tissue. The fluid sample can include blood, interstitial fluid, or both.

1 Claim, 5 Drawing Sheets

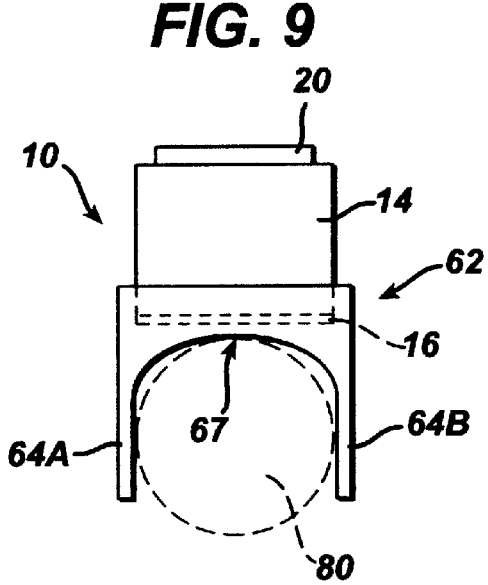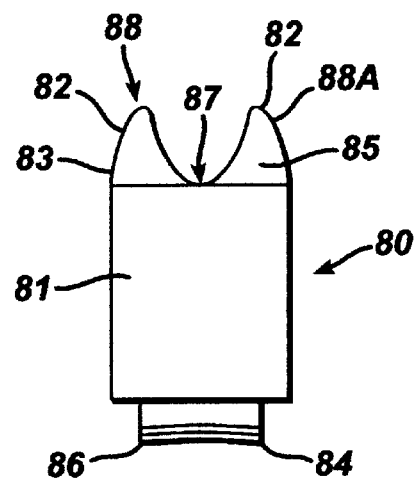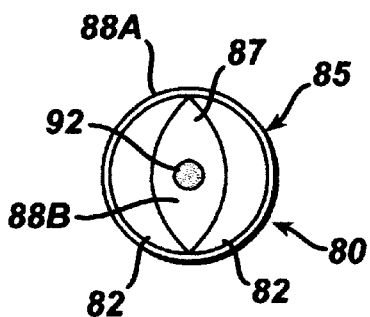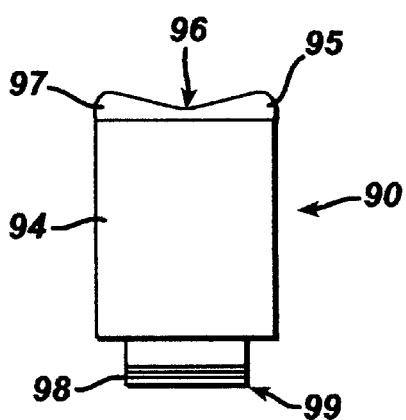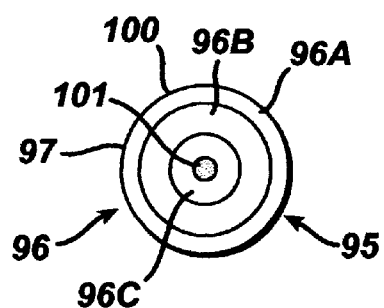

CAP FOR A LANCING DEVICE

RELATED APPLICATIONS

This application claims priority to provisional patent application Ser. No. 60/210,808 filed Jun. 9, 2000 and provisional patent application Ser. No. 60/261,513 filed Jan. 12, 2001, the contents of which are hereby incorporated by reference.

BACKGROUND OF THE INVENTION

The present invention generally relates to lancing devices for lancing dermal tissue and for withdrawing a fluid sample.

Lancets in conventional use generally have a rigid body and a sterile needle which protrudes from one end. The lancet may be used to pierce the skin, thereby enabling the collection of a blood sample from the opening. The blood is then transferred to a test collection device. Blood is most commonly taken from the fingertips, where there is generally an abundant supply. However, the nerve density in this region causes significant pain in many patients. Sampling of alternate sites, such as earlobes and limbs, is sometimes practiced to access sites which are less sensitive. These sites are also less likely to provide sufficient blood volume, and make blood transfer directly to test devices difficult.

Repeated lancing in limited surface areas (such as fingertips) results in callous formation. This leads to increased difficulty in drawing blood and increased pain to the user. To reduce the anxiety of piercing the skin and the associated pain, many spring loaded devices have been developed.

After puncturing the skin, conventional lancing devices are laid down and the free hand of the user squeezes blood from the puncture wound. This technique requires a clean storage site for the lancing device and a two-hand operation. Once the drop of blood is expressed from the lancing site, the user transfers the blood to a test strip of a suitable meter.

It is often desirable to collect the expressed sample from the patient and then introduce the sample to a test device in a controlled fashion. Some blood glucose monitoring systems, for example, require that the blood sample be applied to a test device which is in contact with a test instrument. In such situations, bringing the finger of a patient directly to the test device poses some risk of contamination from blood of a previous patient. With such systems, particularly in hospital settings, it is common to lance a patient, collect a sample in a micropipette via capillary action and then deliver the sample from the pipette to the test device.

However, these lancet devices do not extract ('squeeze out') a sufficient sample from the various surfaces for lancing. For example, the curved surface of a fingertip requires the right amount of pressure to be applied to extract blood quickly and efficiently from the patient. Therefore, there is a need for a lancet system that can accommodate the lancing of curved surfaces (e.g., fingertips) as well as flat surfaces (e.g., forearm or leg) to express sufficient volume of blood or interstitial fluid, while concomitantly reducing pain experienced by the user.

SUMMARY OF THE INVENTION

The present invention provides a cap for a lancing device for lancing dermal tissue. The cap includes a cap body having a proximal end for connecting to the distal end of the housing of the lancing device and a contact ring attached to the distal end of the cap body. The contact ring includes an opening for a portion of the lancet of the lancing device to pass therethrough. The contact ring has a multi-contoured surface oriented generally about an axis distinct from the axis of motion of the lancet. The multi-contoured surface is designed to pressure the dermal tissue to facilitate expression of a fluid sample after lancing the dermal tissue. The fluid sample can include blood, interstitial fluid, or both.

In accordance with one aspect of the present invention, the cap body is transparent to facilitate viewing of the quantity of blood expressed.

In accordance with another aspect of the present invention, the multi-contoured surface comprises an outer radial portion oriented at a first angle relative to the axis of the contact ring and an inner radial portion proximate the opening and oriented at a second angle, distinct from the first angle, relative to the axis of the contact ring.

In accordance with a further aspect of the present invention, the cap is removably and replaceably connected to the distal end of the housing.

In accordance with another aspect of the present invention, a sleeve can be mounted about the cap body. The sleeve can be movable generally along the axis of motion of the lancet and relative to the cap body. The sleeve includes at least two legs for maintaining contact with the dermal tissue during expression of a blood sample after lancing the dermal tissue. In addition, the sleeve can be biased toward the distal end of the cap body, for example, by a spring.

In accordance with another aspect of the present invention, the cap body includes a contact ring having a multi-contoured surface oriented to create a radially inwardly extending pressure-gradient, which extends towards a central aperture.

In accordance with another aspect of the present invention, a cap for lancing curved dermal tissue is provided. The contact ring portion of the cap is comprised of a flexible material. The flexible material when placed against the lancing site conforms to the surface, and hence accommodates lancing of the curved dermal tissue to create a pressure gradient beneath the skin to express a suitable fluid sample. This flexible cap creates a pressure gradient and expresses dermal fluid on strongly curved and flat areas of the skin without having to change the cap or use a different lancing device.

In accordance with yet another aspect of the present invention, a lancing device for lancing dermal tissue is provided. The lancing device includes a housing, a lancet and a cap. The cap includes a cap body and a contact ring having a multi-contoured surface oriented generally about an axis distinct from the axis of motion of the lancet. The multi-contoured surface is designed to pressure the dermal tissue to facilitate expression of a fluid sample after lancing the dermal tissue. The fluid sample can include blood, interstitial fluid, or both.

BRIEF DESCRIPTION OF THE DRAWINGS

These and other features and advantages of the present invention will be more fully understood by reference to the following detailed description in conjunction with the attached drawings in which like reference numerals refer to like elements through the different views. The drawings illustrate principles of the invention and, although not to scale, show relative dimensions.

FIG. 9 is a front elevational view of the cap of FIG. 5;

FIG. 10 is a front elevational view of another embodiment of a cap for a lancing device, suitable for lancing a fingertip in accordance with the teachings of the present invention;

FIG. 11 is an end view of the cap of FIG. 10;

FIG. 12 is a front elevational view of another embodiment of a cap for a lancing device for lancing the ventral side of a fingertip in accordance with the teachings of the present invention;

FIG. 13 is an end view of the cap of FIG. 12;

DESCRIPTION OF ILLUSTRATED EMBODIMENTS

Figure 1:
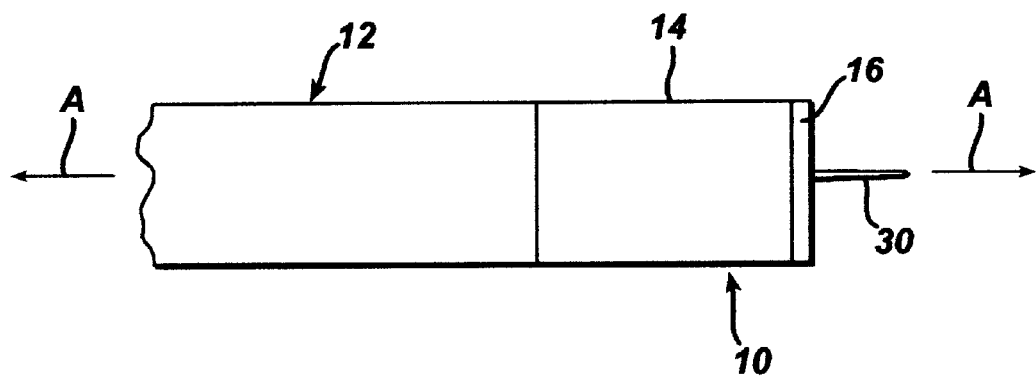
FIG. 1 is a side elevational view of a cap for a lancing device, illustrating the cap attached to a lancing device in accordance with the teachings of the present invention.

The present invention is directed to a cap for use with a lancing device for lancing dermal tissue to express a fluid sample, such as blood, interstitial fluid, or both. We refer below to the expression of blood for purposes of simplicity, although it is intended to encompass the expression of interstitial fluid or both. The cap of the present invention is designed to facilitate the expression of blood after the dermal tissue is lanced by increasing the pressure on the dermal tissue surrounding the lancing site. This increase in pressure results in increased blood flow from the lancing site, thereby reducing the time necessary to express a sufficient quantity of blood and eliminating the need for placing the lancing device on a surface and using the other free hand to squeeze out the sample fluid.

Moreover, the cap of the present invention is particularly suited for collecting blood samples from lancing sites other than on the fingertip of the patient, which is the traditional location for collecting blood samples. Use of such alternative sites can be less painful to the patient and also allows the patient to "rest" his or her fingertip. Suitable alternative sites include, but are not limited to, the forearms, the upper arms, the thighs, the palms, and the abdomen of a patient. Blood sample collection at alternative sites can be problematic as manually applying sufficient pressure on the dermal tissue proximate the lancing site to collect the blood sample can be difficult and typically results in low yields. The cap of the present invention allows the user to increase the amount of pressure at the lancing site such that a sufficient quantity of blood can be expressed from the alternative sample site.

A cap 10 in accordance with one preferred embodiment of the present invention is illustrated in FIGS. 1 through 4. The cap 10 is design to be connected to the distal end of the housing 12 of a conventional lancing device. In a conventional lancing device a lancet 30 is mounted within the housing 12 of the lancing device and is movable along a first axis, indicated by line A in FIG. 1, relative to the housing 12. The lancet 30 can be driven along the first axis by the lancing device to puncture the dermal tissue. The blood sample can then be expressed for collection from the lancing site. Such conventional lancing devices are available from Lifescan, Inc. of Milpitas, Calif., Palco Laboratories of Santa Cruz, Calif., Therasense of Alameda, Calif., and Amira Medical of Scotts Valley Calif. In addition, lancing devices are described in U.S. Pat. Nos. 5,730,753 to Morita, U.S. Pat. No. 6,045,567 to Taylor, and U.S. Pat. No. 6,071,250 to Douglas. Each of the aforementioned patents is incorporated herein by reference. One skilled in the art will appreciate that the cap of the present invention is not limited to the lancing devices described herein. The cap of the present invention can be used with any lancing device employing a movable lancet for lancing dermal tissue. Moreover, the present invention is intended to include any device suitable for expressing a fluid sample from a user employing different extraction techniques, including the use of lancets, hollow and solid needles or microneedles, ultrasonic devices, thermal techniques, and the like. The device can be a simple lancing device as described above, or can include devices having integrated meters or measuring devices suitable for testing an analyte, such as glucose.

Figure 2:
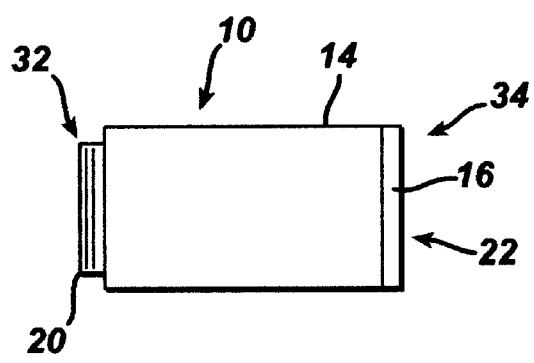
FIG. 2 is a side elevational view of the cap of FIG. 1.

The cap 10 includes a cap body 14 having a proximal end 32 and a distal end 34 as best illustrated in FIG. 2. A contact ring 16 is attached to the distal end 34 of the cap body 14. An opening 18, shown in FIGS. 3A and 4A, is provided in the contact ring 16 to allow a portion of the lancet 30 to pass therethrough to effect puncturing of the dermal tissue.

Referring to FIG. 2, the cap body 14 can include a connector 20 for removably and replaceably connecting the proximal end 32 of the cap body 14 to the distal end of the housing 12 of the lancing device. The connector 20 preferably is threaded to mate with corresponding threads provided in the housing 12 of the lancing device. One skilled in the art will recognize that alternative connecting mechanisms may be used without departing from the scope of the present invention. For example, the connector 20 can be sized and shaped to snap-fit to the housing 12. In addition, the cap 10 can be permanently affixed to the housing 12, although, it is preferable for the cap 14 to be removably and replaceably connected to the housing 12.

The cap body 14 can be constructed from a transparent, translucent or opaque material, such as a clear, transparent plastic, or includes a transparent portion forming a window to the interior of the cap body, or can be constructed of conventional non-transparent material. If transparent, the material should be sufficiently so to permit expressed blood to be viewed within the cap body 14. The transparency of the cap body 14 allows the user to view the amount of blood expressed for collection from the lancing site, as discussed in more detail below.

Figure 3A:
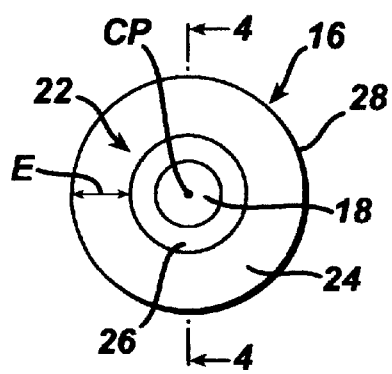
FIG. 3A is an end view of the cap of FIG. 1.
Figure 4A:
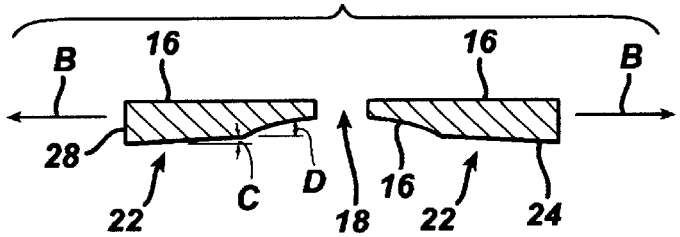
FIG. 4A is a side elevational view in cross section along line 4—4 of FIG. 3, illustrating the contact ring of the cap of FIG. 3.

Referring to FIGS. 3A and 4A, the contact ring 16 preferably has a multi-contoured surface 22 for contacting the dermal tissue both during lancing and during blood sample expression. The multi-contoured surface 22 is oriented generally about a second axis, indicated by line B in FIG. 4A, distinct from the first axis A. In the preferred embodiment described herein the second axis B is perpendicular to the first axis A. One skilled in the art will recognize that the second axis is not limited to this preferred orientation and that any orientation distinct from the axis of motion of the lancet can be employed.

The multi-contoured surface 22 is designed to pressure the dermal tissue to maximize blood flow rate from the periphery of the pressured area to the center of the lancing site and to facilitate the expression of a blood sample for collection. The term multi-contoured surface as used herein is intended to include two or more surfaces oriented at distinct angles with respect to each other and with respect to a common axis. The multi-contoured surface can extend inwardly from a vertical wall, or can extend inwardly from a flat surface extending radially inwardly from the vertical wall. Those of ordinary skill will recognize that the multi-contoured surface can include any selected number of surfaces. The surface can be, according to one practice, non-planar. In one embodiment described herein, the multi-contoured surface 22 is comprised of an outer radial portion 24 and an inner radial portion 26 proximate the opening 18. The outer radial portion 24 is preferably oriented at a first angle C relative to the second axis B. The inner radial portion 26 is preferably oriented at a second angle D, distinct from the first angle C, relative to the second axis B. The outer radial portion 24 and the inner radial portion 26 can have any selected surface feature or shape, e.g., can be linear, stepped, or curved. In the illustrated embodiment, the outer radial portion 24 is generally linear from the perimeter 28 of the contact ring 16 to the intersection with the inner radial portion 26. Alternatively, the outer radial portion 24 can be convex or concave in curvature. Additionally, the inner radial portion 26 is generally concave in curvature, but can also be linear or convex.

As shown in FIG. 4A, the angle C, corresponding to the slope of the outer radial portion 24, is in the range between about 5° and about 15°. Additionally, the radial extent of the outer radial portion 24, generally illustrated by line E in FIG. 3A, is preferably between about 25% to about 75% of the total radius of the contact ring 16, as measured from the center point CP of the contact ring 16 to the perimeter 28 of the contact ring 16. In a preferred embodiment, the radial extent E of the outer radial portion 24 is preferably about 50% of the total radius of the contact ring 16.

The contact ring 16 can be constructed from plastic or other materials suitable for use in a medical instrument. The contact ring 16 can have a non-transparent color, such as white, that is distinct and in contrast from the color of the dermal tissue. A contrasting color allows the user to better visualize the quantity of expressed blood.

The contact ring 16 can be a separate, discrete component affixed to the cap body 14, or can be integrally formed with the cap body 14.

Figure 4B:
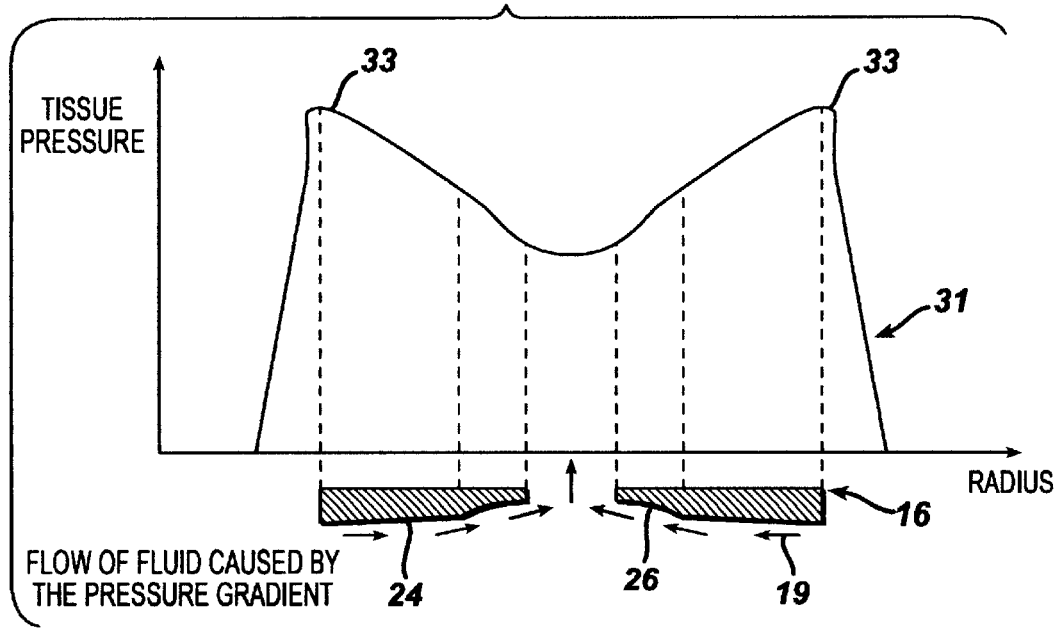
FIG. 4B is a graphic representation of the pressure profile created by the cap of FIG. 2.

With reference to FIG. 4B, the contact ring 16 of the cap 10 is sized and dimensioned to be placed in intimate facing contact with the skin of the user. When placed thereagainst, the contact ring creates a pressure gradient that extends from the radial outer surface inwardly towards the opening 18. Specifically, when the skin is lanced by the lancet 30, the contact ring 16, which is disposed about the lancing site, creates a pressure gradient that urges fluid to flow toward the opening 18, as indicated by arrows 19.

The pressure profile 31 created by the cap 10 has pressure peaks 33 that coincide with the perimeter portion of the cap, or with the start of the multi-contoured surface 22. The pressure is a maximum at this portion since the cap contacts the skin of the user to a greater degree. When the surfaces of the multi-contoured surface extend inwardly towards the opening 18 and away from the skin, the overall pressure decreases. This forms a pressure gradient that extends from the outermost portion of the cap 10 to the opening 18. The illustrated pressure gradient 31 has decreases in a somewhat uniform manner across the surface 24, and in a more rapid manner across surface 26. Those of ordinary skill will recognize that the pressure profile will change as a function of the configuration of the contact ring.

Figure 3B:
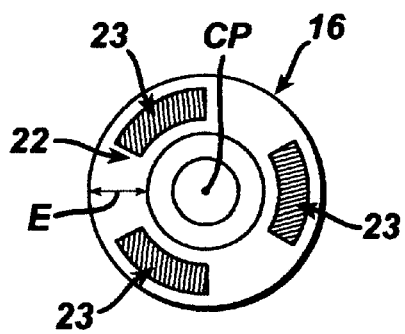
FIG. 3B is an end view of the cap of FIG. 1, wherein an anti-slip material is affixed to the contact ring.

According to an alternative embodiment of the invention, illustrated in FIG. 3B, the contact ring 16 can include an anti-slip feature adapted to prevent the contact ring 16 and the cap 10 from moving relative to (or across) the surface of the skin during expression of a blood sample. According to one embodiment, the anti-slip feature comprises a suitable anti-slip material 23, such as rubber or silicone, that is attached, coupled or affixed to a portion of the multi-contoured surface 22 of the contact ring. The anti-slip material 23 ensures sufficient friction between the contact ring and the skin to resist movement of the contact ring relative to the skin surface. According to an alternate embodiment, the multi-contoured surface can be formed to have selected surface features, such as protrusions or indentations, or can be roughened, to increase the friction between the contact ring and the skin. Alternatively, the entire contact ring can be formed from an anti-slip material to prevent movement.

Figure 4C:
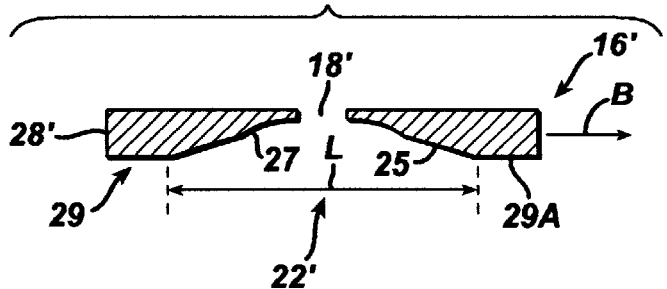
FIG. 4C is a cross-sectional view of an alternate embodiment of the contact ring of the lancing device of the present invention.

FIG. 4C illustrates another embodiment of the contact ring 16 of the cap 10 of the present invention. Like reference numerals designate like or similar parts plus a superscript prime. The illustrated contact ring 16' has an axially or vertically extending outer wall or perimeter 28' that terminates at a distal end 29. The distal end 29 includes a first flat face portion 29A that is adapted to press against the skin of the user during use. The flat face portion 29A is generally perpendicular to the perimeter portion 28'. The multi-contoured surface 22' extends radially inwardly from the flat face portion 29A towards the opening 18'. The multi-contoured surface 22' extends between the annular flat face portion 29A, as indicated by the designation L. The multi-contoured surface can also be configured to include the flat face portion 29A. In this embodiment, the multi-contoured surface includes three surfaces. Optionally, an anti-slip feature, comprising an anti-slip material or a roughened surface, may be incorporated in the contact ring 16' to prevent movement of the contact ring relative to the skin surface during expression of the blood sample.

The illustrated multi-contoured surface 22' includes two or more surfaces oriented relative to each other to form different, distinct angles. In particular, the multi-contoured surface 22' includes a pair of surfaces 25 and 27. The radially outer surface 25 is oriented at a first angle relative to the axis B. The radially inner surface 27 is oriented at a second angle relative to the axis B different from the first angle. As described above, the surfaces 25 and 27 can have any selected shape or angle.

In use, the cap 10 is connected to the housing 12 of the lancing device and the dermal tissue is lanced by the lancet 30 passing through the opening 18 in the contact ring 16. The lancet 30 is then withdrawn into the cap 10 or the lancing device. The contact ring 16 is pressed into contact with the dermal tissue proximate the lancing site causing blood to exit the lancing site and enter the cap 10 through the opening 18. Dermal tissue is "squeezed" into contact with the outer radial portion 24 and the inner radial portion 26 of the multi-contoured surface 22. The multi-contoured surface 22 facilitates blood expression by increasing the hydrostatic pressure on the dermal tissue in contact with the perimeter 28 of the contact ring 16. The hydrostatic pressure on the dermal tissue decreases as the slope of the outer radial surface 24 and the inner radial surface changes toward the opening 18. This inwardly extending pressure gradient is illustrated in FIG. 4B. Experimental testing has revealed that 1.5 ml to 3 ml of blood can easily be expressed from the lancing site using the cap 10 of the present invention at sampling sites other than the finger. In addition, because the cap body 14 can be transparent and the contact ring can be a contrasting color, such as white, the user can easily monitor the volume of blood expressed.

An alternative embodiment of the cap of the present invention is illustrated in FIGS. 5 through 9, in which a sleeve 60 is mounted about the cap body 14. The sleeve 60 is movable generally along the first axis A, i.e., along the axis of motion of the lancet, and relative to the cap body 60. The sleeve 60 comprises an annular collar 62 and at least two legs 64A and 64B that extend from the collar 62 in the direction of the first axis A toward the distal end 34 of the cap 10. The legs 64A and 64B taper from an increased width proximate the collar 62 to a decreased width proximate the contact ring 16.

Figure 6:
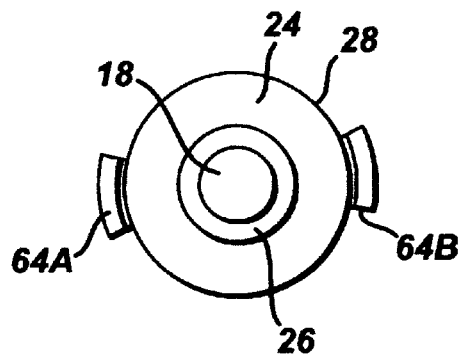
FIG. 6 is an end view of the cap of FIG. 5.

As illustrated in FIG. 6, the legs 64A and 64B are arcuate in cross-section and encompass only a portion of the circumference of the contact ring 16. The legs 64A and 64B are preferably symmetrically disposed about the circumference of the contact ring 16. Although only two legs are illustrated, one skilled in the art will appreciate that additional legs can be added without departing from the present invention. In addition, the legs need not be positioned symmetrically about the contact ring 16.

Figure 5:
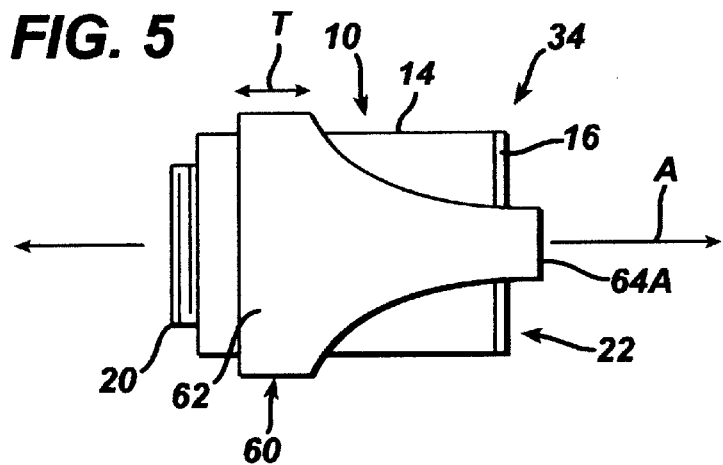
FIG. 5 is a side elevational view of an alternative embodiment of the cap for a lancing device of the present invention, illustrating a sleeve positioned about the cap in accordance with the teachings of the present invention.

The sleeve 60 is preferably slidable along an axis parallel to the first axis A, as indicated by arrow T in FIG. 5. A longitudinally extending slot 66 can be formed in one or both of sides of the cap body 14. A protruding guide member 68 can be formed in one or both of the legs 64A and 64B. The guide member 68 is sized and shaped to slide within the slot 66 and inhibits lateral motion of the sleeve 60 relative to the cap body 14. Alternatively, the slot 66 can be formed in one or more of the legs 64A and 64B and the guide member 68 can be formed on the cap body 14.

A spring 70 or other biasing mechanism can be provided to bias the sleeve 60 toward the distal end of the cap 10. One skilled in the art will appreciate that the sleeve 60 is not limited to use with the cap 10 of the present invention, but can be used with the cap of any lancing device.

Figure 7:
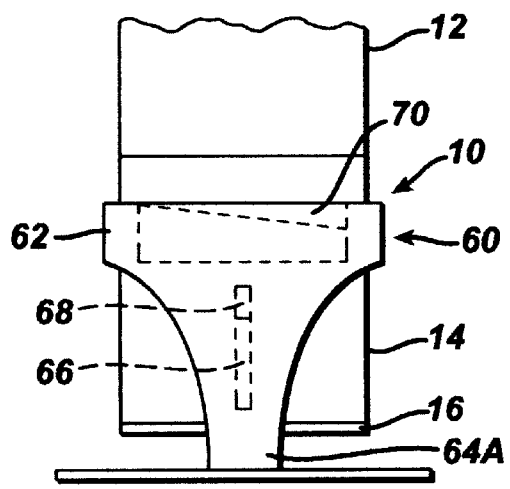
FIG. 7 is a side elevational view of the cap of FIG. 5, illustrating the cap displaced from the skin in accordance with the teachings of the present invention.
Figure 8:
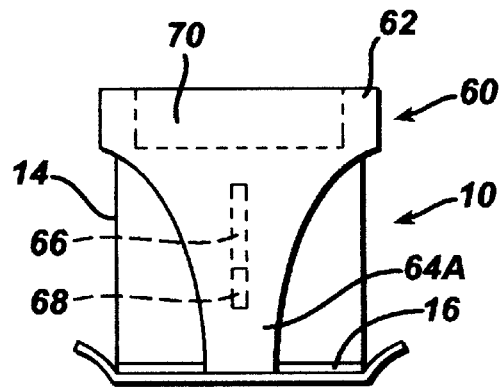
FIG. 8 is a side elevational view of the cap of FIG. 5, illustrating the cap in contact with the skin in accordance with the teachings of the present invention.

It is sometimes desirable to remove the cap 10 and the contact ring 16 from contact with the dermal tissue after lancing, for example, to remove pressure from the dermal tissue or to visibly inspect the lancing site. The sleeve 60 allows the user to maintain a portion of the lancing device, the legs 64A and 64B of the sleeve 60, in contact with skin when the cap 14 and the contact ring 16 are removed from contact with skin, as illustrated in FIG. 7. Importantly, the legs 64A and 64B allow the user to maintain the opening 18 in alignment with the lancing site when the contact ring is returned into contact with dermal tissue, as illustrated in FIG. 8. According to one embodiment, the sleeve legs 64A and 64B further include an anti-slip feature to prevent movement of the sleeve relative to the skin. An anti-slip material, such as rubber or silicone, may be affixed to the contact surface of the sleeve legs to prevent movement. Alternatively, the anti-slip feature comprises a roughened surface where the sleeve legs contact the skin.

Referring to FIG. 9, the legs 64A and 64B can be spaced apart a distance sufficient to allow a finger 80 of the user to fit between the legs 64A and 64B. The surfaces 67 connecting the two legs 64A and 64B can be curved, and are preferably parabolic in shape, to further facilitate the user's finger 80. In addition, the legs 64A and 64B, as well as the sleeve 60, can be constructed from a flexible, resilient material, such as a flexible plastic. The preferred material of choice is ABS plastic. As illustrated in FIG. 9, the user's finger 80 can be positioned between the legs 64A and 64B when the sleeve 60 is positioned beneath the cap 10. The legs 64A and 64B compress the user's finger therebetween to pinch or squeeze the dermal tissue. The user's finger can then be lanced and the compression of the user's finger by the legs 64A and 64B can facilitate the expression of blood from the lancing site.

Alternate embodiments of the cap of the present invention are illustrated in FIGS. 10 through 13, in which the contact ring 16 is designed for lancing the sharp curve (or side) of the fingertip, as well as the ventral side of the fingertips.

FIGS. 10 and 11 illustrate another embodiment of the cap of the present invention. The cap 80 includes a cap body 81 having a proximal end 86. A contact ring 85 is attached to the distal end 83 of the cap body 81. An opening 92 is provided in the contact ring 85 to allow a portion of the lancet 30 to pass through to effect puncturing of the fingertip. The illustrated cap body 81 can include a connector 84 for removably and replaceably connecting the proximal end 86 of the cap body 81 to the distal end of the housing 12 of the lancing device. For example, the connector 84 can be sized and shaped to fit the housing 12. The cap 80 can be permanently affixed to the housing 12, although it is preferable that the cap 80 be removably and replaceably connected to the housing 12.

The cap body 81 is constructed from transparent, translucent, or opaque material, such as clear or transparent plastic, or includes a transparent portion forming a window to the interior of the cap body. The material should be sufficiently transparent to allow the blood being expressed from within the cap body 81 to be viewed by the user. The transparency of the cap body 81 allows the view the amount of blood expressed for collection from the lancing, etc.

The contact ring 85 preferably employs a pair of pressure wings 82 sized and dimensioned to accommodate the sharp curve of the fingertip therebetween. The pressure wings 82 thus form a recess 87 for accommodating the finger of the user. This applies the correct amount of pressure to allow for the expression of blood.

Referring to FIG. 11, the pressure wings extend radially outward and away from the contact ring for contacting the fingertip both during lancing and during blood sample by pressing. The pressure wings 82 and 82 constitute a multi-contoured surface that extends from the outer periphery of the body 81 to the opening 92. The multi-contoured surface 88 is designed to pressure the fingertip to maximize blood flow rate from the lancing site and to facilitate the expression of blood for sample collection. The illustrated multi-contoured surface 88 comprises two or more non-planar surfaces disposed at distinct angles relative to each other and with respect to a common axis. For example, the pressure wings 82, 82 that constitute the multi-contoured surface 88 is comprised of a radial outer portion 88A and a curved radial inner portion 88B proximate to the opening 92. The transition point between the surfaces 88A and 88B can be arcuate, rounded, or sharp.

The illustrated contact ring 85 can be constructed from plastic or other materials suitable for use in a medical instrument. The contact ring 85 can have a nontransparent color that is distinct from the color of the fingertip. White is the preferred color of choice. A contrasting color allows the user to better visualize the quantity of blood expressed. The contact ring 85 can be a separate, discrete component affixed to the cap body 81, or can be integrally formed with the cap body 81.

When in use, the cap 80 is connected to the housing 12 of the lancing device, and the fingertip of the user is placed in the recess 87 formed by the pressure wings 82, 82. The lancet 30 of the device is deployed and passes through the opening 92 in the contact ring 85 to pierce the skin. The contact ring 85 is pressed into contact with the fingertip proximate to the lancing site to express blood. The multi-contoured surface 87 facilitates blood expression by creating a pressure gradient that extends radially inwardly towards the opening 92. According to an alternate embodiment, an anti-slip feature on the contact ring 85 prevents movement of the contact ring relative to the skin surface when the contact ring is pressed into contact with the fingertip. As discussed, the anti-slip feature can comprise a suitable anti-slip material affixed to the multi-contoured surface, or a roughened multi-contoured surface. Alternatively, the contact ring 85 can be constructed entirely of a suitable anti-slip material to provide an anti-slip feature.

FIGS. 12 and 13 illustrate another embodiment of the cap according to the teachings of the present invention. As illustrated in FIG. 12, the cap 90 includes a contact ring 95 attached to the distal end 97 of the cap body 94. An opening 124 formed in the contact ring 95 allows a portion of the lancet 30 to pass therethrough to create a puncture on the ventral side of the fingertip.

The cap body 94 includes a connector 99 for removably and replaceably connecting a proximal end 98 of the cap body 94 to a distal end of the housing 12. For example, the connector 99 can be sized and shaped to fit the housing 12. Also, the cap 90 can be permanently affixed to the housing 12. Preferably, the cap 93 is removably and replaceably connected to the housing 12. The cap body 94 is preferably similar to cap body 81 of FIG. 10. The materials of cap 80 are also the same for cap 93. The material can be transparent or include a transparent portion to allow expressed blood to be viewed within the cap 93.

The illustrated contact ring 95 has a multi-contoured surface 96 that extends from the periphery of the cap body 94 to the central opening 101. The multi-contoured surface 96 can include two or more surfaces disposed at distinct angles relative to each other and with respect to a common axis. For example, the illustrated multi-contoured surface 96 is comprised of an outer radial portion 96A, a middle portion 96B, and an inner radial portion 96C disposed proximate to the opening 101. The outer, middle and inner radial portions of the cap can have any selected surface feature or shape, e.g., can be linear, stepped, or curved. Moreover, the transition points between each surface 96A, 96B and 96C of the multi-contoured surface can have rounded, arcuate, or sharp surface features.

The illustrated contact ring 95 can be constructed from plastic or other materials suitable for use in a medical instrument. The contact ring 95 can have a non-transparent color that is distinct from the color of the fingertip. White is the preferred color of choice. A contrasting color allows the user to better visualize the quantity of blood expressed. Similarly to cap 80, the contact ring 95 can be separated, discrete component affixed to the cap body 94, or can be integrally formed with the cap body 94.

When in use, the cap 90 is connected to the housing 12 of the lancing device and the fingertip is placed in intimate facing contact with the ventral side finger and lanced by the lancet 30 passing through the opening 101 in the contact ring 96. The lancet 30 is withdrawn into the cap 90 or lancing device. The fingertip is squeezed into contact with the outer radial portion 96A, middle radial portion 96B, and inner radial portion 96C of the multi-contoured surface 96. The multi-contour surface 96 facilitates blood expression by creating a pressure gradient that extends radially inwardly toward the opening 101 from the perimeter 100 of the contact ring 95 or cap body 94. According to one embodiment, an anti-slip feature on the contact ring 95 prevents movement of the contact ring relative to the skin surface when the contact ring is pressed into contact with the fingertip. As discussed, the anti-slip feature can comprise a suitable anti-slip material, such as rubber or silicone, affixed to the multi-contoured surface. Alternatively, at least a portion of the multi-contoured surface comprises a roughened contact surface to ensure friction between the contact ring and the skin.

An alternative embodiment of the cap of the present invention is illustrated in FIGS. 14–17 in which the contact region is designed with a flexible material for lancing various surfaces of a user.

Figure 14:
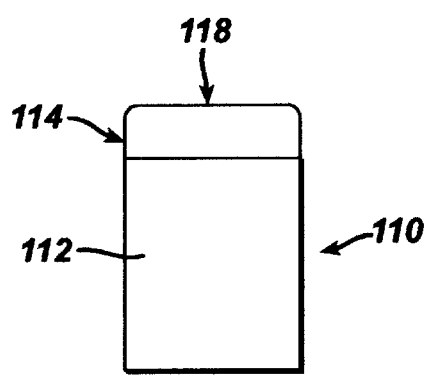
FIG. 14 is a side view of an alternate embodiment of the cap of the present invention formed of a flexible material and disposed in a rest position.
Figure 15:
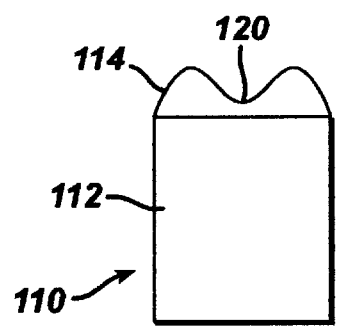
FIG. 15 is a side view of the cap of FIG. 14 when the contact ring contacts the lancing site.

FIGS. 14 and 15 illustrate another embodiment of the cap for use at multiple different lancing sites according to the teachings of the present invention. The illustrated cap 110 includes a cap body 112 that terminates at a contact ring 114 mounted at a distal end. The distal end 115 of the cap 110 can couple to the housing 12 via any suitable structure. According to a preferred embodiment, the cap is permanently affixed to the housing, and hence not axially movable relative thereto. The contact ring 114 of the cap 110 can include, if desired, a multi-contoured surface 118 having a plurality of surfaces oriented at angles relative to each other. A central opening can also be formed therein. According to an alternate embodiment, the contact ring can be a unitary structure with nominal surface features formed therein.

The illustrated contact ring is preferably formed of a deformable, resilient, flexible material that is capable of conforming to the shape of the body region of the user placed in contact therewith. The contact ring can be preferably formed of a rubber material, polyurethane, latex, or other flexible material. The cap body 112 can also be formed of any suitable transparent, translucent, or opaque material, such as clear or transparent plastic, or can include a transparent portion forming a window to the interior of the cap body to enable the user to view the expressed blood. Alternatively, the cap can be formed of a non-transparent material.

The contact ring 114 can be disposed in a rest position, FIG. 14, when not in contact with a lancing site, and hence no shape is imparted to the ring. When placed in contact with the lancing site, such as the ventral side of a finger, or any other suitable portion of the finger, the contact ring conforms to the shape of the lancing site, FIG. 15. According to one embodiment, an anti-slip feature on the contact ring 114 prevents movement of the contact ring relative to the skin surface when the contact ring is pressed into contact with the fingertip. As discussed, the anti-slip feature can comprise a suitable anti-slip material, such as rubber or silicone, affixed to the multi-contoured surface. Alternatively, at least a portion of the multi-contoured surface comprises a roughened contact surface to ensure friction between the contact ring and the skin.

Figure 16:
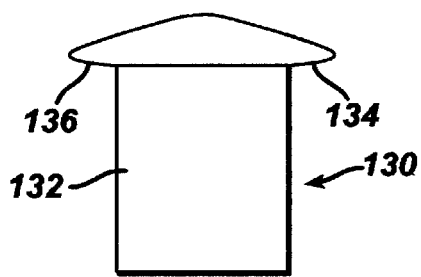
FIG. 16 is a side view of an alternate embodiment of the cap of the present invention formed of a deformable, flexible material and disposed in a rest position.
Figure 17:
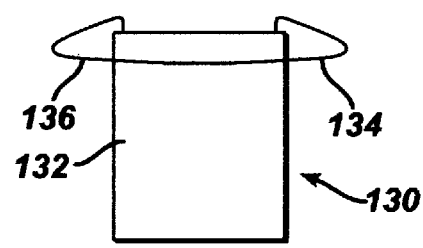
FIG. 17 is a side view of the cap of FIG. 16 when the contact ring contacts the lancing site.

According to an alternate embodiment, as illustrated in FIGS. 16 and 17, a cap 130 includes a cap body 132 that has mounted thereto a deformable contact ring 134. The illustrated contact ring 134 has edge portions 136 that extend over or outwardly from the perimeter of the cap body 132. The contact ring can include, if desired, a multi-contoured surface having a plurality of surfaces oriented at angles relative to each other. A central opening can also be formed therein. According to an alternate embodiment, the contact ring can be a unitary structure with nominal surface features formed therein.

The contact ring can be preferably formed of rubber material, polyurethane, latex, or other flexible material. The contact ring 134 can be disposed in a rest position, FIG. 16, when not disposed in contact with a lancing site, and hence no shape is imparted to the ring. When placed in contact with the lancing site, such as the ventral side of a finger, or any other suitable portion of the finger, the contact ring 134 conforms to the shape of the lancing site, FIG. 17. Moreover, when disposed in this position, the overhanging portions of the deformable contact ring, can 'flip' over and extend along the outer surface of the cap body 132 so it can be used on a flatter skin area, such as the forearm.

The cap body 132 can includes a connector for removably and replaceably connecting a proximal end of the cap body 132 to a distal end of the housing 12. According to one practice, the cap 130 can be permanently affixed to the housing 12. Preferably, the cap 130 is removably and replaceably connected to the housing 12.

Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

What is claimed is:

1. A cap for a lancing device for lancing dermal tissue, the lancing device including a housing having a proximal end and a distal end and a lancet mounted within the housing, the lancet being movable along a first axis relative to the housing, the cap comprising:

a cap body having a proximal end and a distal end, and proximal end of the cap body connecting to the distal end of the housing of the lancing device;

a contact ring attached to the distal end of the cap body, the contact ring having a multi-contoured surface oriented generally about a second axis distinct from the first axis for pressuring the dermal tissue to facilitate expression of a blood sample after lancing the dermal tissue; and wherein the multi-contoured surface comprises a pair of pressure wings.

* * * * *